United States Patent [19]

Pelster et al.

[11] 4,038,328

[45] July 26, 1977

[54] PROCESS FOR PREPARING 2-NITRO-4,6-DICHLORO-5-METHYL-PHENOL

[75] Inventors: Heinrich Pelster, Odenthal-Gloebusch; Uwe Beck, Cologne, both of Germany

[73] Assignee: Bayer Aktiengesellschaft, Leverkusen, Germany

[21] Appl. No.: 645,983

[22] Filed: Jan. 2, 1976

[30] Foreign Application Priority Data

Jan. 18, 1975 Germany .............................. 2501899

[51] Int. Cl.$^2$ .................... C07C 79/32; C07C 39/26
[52] U.S. Cl. .......................... 260/622 R; 260/623 R; 260/505 R; 260/512 R
[58] Field of Search ........... 260/622 R, 505 R, 512 R, 260/623 H

[56] References Cited

U.S. PATENT DOCUMENTS 2,249,757   7/1941   Flett .................................. 260/512 R
3,903,178   9/1975   Nakamura et al. ............... 260/622 R

*Primary Examiner*—Bernard Helfin
*Assistant Examiner*—W. B. Lone
*Attorney, Agent, or Firm*—Burgess, Dinklage & Sprung

[57] ABSTRACT

2-nitro-4,6-dichloro-5-methylphenol is prepared by the sulfonation of 4-chloro-5-methylphenol to form 2-sulfo-4-chloro-5-methylphenol which is chlorinated to 2-sulfo-4,6-dichloro-5-methylphenol which is in turn reacted with nitric acid to form the desired product. The sulfonation is carried out with concentrated sulfuric acid at elevated temperatures to form 2-sulfo-4-chloro-5-methylphenol. Thereafter the reaction mixture is diluted with water to a sulfuric acid content of 20-30%. The resulting 2-sulfo-4-chloro-5-methylphenol is chlorinated with chlorine at elevated temperature and normal or elevated pressures to form 2-sulfo-4,6-dichloro-5-methylphenol which is then reacted with nitric acid.

4 Claims, No Drawings

PROCESS FOR PREPARING 2-NITRO-4,6-DICHLORO-5-METHYLPHENOL

BACKGROUND

This invention relates to a process for the preparation of 2-nitro-4,6-dichloro-5-methylphenol.

It is known that 2-nitro-4,6-dichloro-5-methylphenol can be prepared (German Published Specification) No. 2,216,804 by sulphonating 4-chloro-5-methylphenol with a sulphuric acid anhydride complex in a halogenated hydrocarbon as the solvent, to form 2-sulpho-4-chloro-5-methylphenol, chlorinating this 2-sulpho-4-chloro-5-methylphenol, for example with chlorine, to form 2-sulpho-4,6-dichloro-5-methylphenol and reacting this 2-sulpho-4, 6-dichloro-5-methylphenol with a nitrating agent.

SUMMARY

According to the present invention there is provided a process for preparing 2-nitro-4,6-dichloro-5-methylphenol comprising sulphonation of 4-chloro-5-methylphenol with concentrated sulphuric acid at elevated temperature to form 2-sulpho-4-chloro-5-methylphenol, thereafter diluting the reaction mixture with water to a sulphuric acid content of 20 to 30%, chlorinating the resulting 2-sulpho-4-chloro-5-methylphenol with chlorine at elevated temperature and normal or elevated pressure to form 2-sulpho-4,6-dichloro-5-methylphenol and reacting the 2-sulpho-4,6-dichloro-5-methylphenol with nitric acid.

DESCRIPTION

The sulphonation of 4-chloro-5-methylphenol, as the first stage of the process, can be illustrated by the following equation:

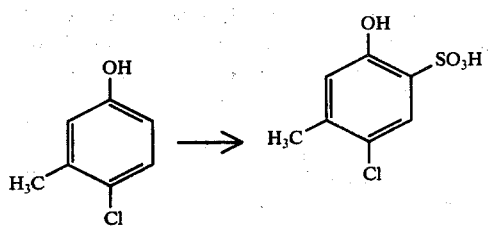

The chlorination of the 2-sulpho-4-chloro-5-methylphenol, prepared in the first stage, in the second stage of the process can be illustrated by the following equation:

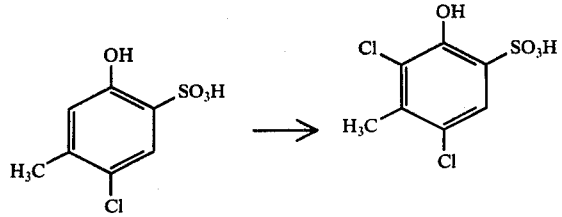

The reaction of the 2-sulpho-4,6-dichloro-5-methylphenol, prepared in the second stage, with nitric acid in the third process stage to give 2-nitro-4,6-dichloro-5-methylphenol can be illustrated by the following equation:

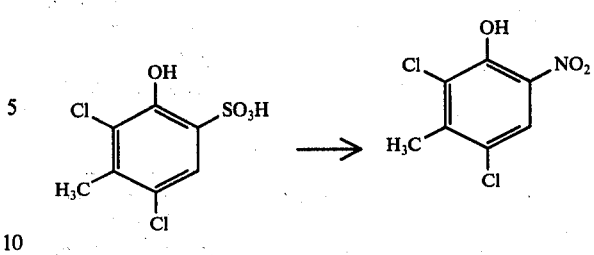

According to the process of the invention, the sulphonation of 4-chloro-5-methylphenol is carried out with concentrated sulphuric acid. The sulphuric acid can be of 80 to 100% strength by weight, preferably 95 to 98% strength by weight. The amount of sulphuric acid employed is not critical; however, to achieve a quantitative reaction at least an equivalent amount of sulphuric acid, based on the starting compounds, is required. For example, sufficient sulphuric acid is employed in the reaction to dissolve the starting compound completely and produce a reaction mixture which is readily stirrable. To achieve the optimum course of the reaction, preferably 5 to 7 mols of sulphuric acid can be employed, relative to the starting compound.

The sulphonation according to the process of the invention can be carried out at 40 to 100° C, preferably at 50° to 60° C.

The reaction time depends on the temperature and can be from 2 to several hours, without decreasing the yield.

According to the process of the invention, the reaction mixture is diluted with water after the sulphonation. For example, sufficient water is added to the reaction mixture to give a sulphuric acid of 20 to 30% strength by weight, preferably 24 to 26% strength by weight.

According to the process of the invention, the chlorination of 2-sulpho-4-chloro-5-methylphenol can be carried out in dilute sulphuric acid by means of chlorine.

The amount of chlorine employed in accordance with the process of the invention can be 1 to 2 times, preferably 1.01 to 1.1 times, in relation to the starting compounds.

The chlorination according to the process of the invention can be carried out at temperatures of 45° to 60° C, preferably 50° to 55° C, and pressures of 1 to 3 bars, preferably 1.4 to 1.9 bars.

The nitration of 2-sulpho-4,6-dichloro-5-methylphenol to give 2-nitro-4,6-dichloro-5-methylphenol can be effected in a conventional manner by replacing the sulpho group by the nitro group by means of nitric acid. The replacement can be carried out by addition of 1.1 to 1.3 times the molar amount of nitric acid at a temperature of 25 to 40° C, preferably of 30 to 35° C.

Generally, the process can be carried out as follows:

In the first process stage, the 4-chloro-5-methylphenol is dissolved in an excess of concentrated sulphuric acid and the reaction mixture is brought to the reaction temperature whilst stirring.

After completion of the reaction, the reaction mixture is forced onto water and in a second reaction step the chlorination to give 2-sulpho-4,6-dichloro-5-methylphenol is carried out in the dilute sulphuric acid. The hydrogen chloride produced in the chlorination dissolves in the dilute sulphuric acid and does not have to be removed separately.

In the third process step, nitric acid is added, with slight warming and without intermediate isolation of the 2-sulpho-4,6-dichloro-5-methylphenol produced in the second process step. The reaction product can be separated off by, for example, filtration.

The process according to the invention permits the preparation of 2-nitro-4,6-dichloro-5-methylphenol from 4-chloro-5-methylphenol in one reaction medium, without isolating an intermediate product. The process can be carried out in a technically simple manner and with high yields. The hydrogen chloride produced during the chlorination does not have to be separated off during the reaction by using an expensive absorption system, since the hydrogen chloride remains dissolved in the dilute sulphuric acid while carrying out the process according to the invention.

Hydrogenation of 2-nitro-4,6-dichloro-5-methylphenol gives 2-amino-4,6-dichloro-5-methylphenol in a conventional manner (German Published Specification No. 2,216,804). 2-Amino-4,6-dichloro-5-methylphenol is an intermediate product for the preparation of a colour coupling agent for color paper. The following examples illustrate the invention:

EXAMPLE I 1,300 g of sulphuric acid (100% strength by weight) are warmed to 55° C in a 6 l flask and 320 g of 4-chloro-5-methylphenol are added in portions. The reaction mixture is kept at 55° C for 3 hours, whilst stirring. Then 3300 g of water are added. The chlorination takes place by passing 160 g of chlorine gas over the course of 7 hours into the reaction mixture, warmed to 55° C. To complete the reaction, the mixture is stirred for a further hour and is then cooled to 30° C. At this temperature, 200 g of nitric acid (80% strength by weight) are added dropwise during 2 hours and then the mixture is stirred for 2 further hours to complete the reaction. Thereafter the reaction mixture is cooled to 15° C and the produced 2-nitro-4,6-dichloro-5-methylphenol is filtered off and washed with ice water.

Melting point: 82 – 84° C

Yield: 400 g (corresponding to 80% of theory).

EXAMPLE 2

1,300 g of sulphuric acid (98% strength by weight) are warmed to 50° C in a 1 l flask and 300 g of 4-chloro-5-methylphenol are added in portions. The reaction mixture is kept at 50° C for 5 hours, whilst stirring, and is then poured onto 3,200 g of water in a 6 l flask.

The chlorination is effected by passing 155 g of chlorine gas over the course of 8 hours into the reaction mixture which is warmed to 50° C. To complete the reaction, the mixture is stirred for a further hour and is then cooled to 35° C. At this temperature, 200 g of nitric acid (80% strength by weight) are added dropwise during 60 minutes and then the mixture is stirred for 2 further hours to complete the reaction.

Then the reaction mixture is allowed to cool to 10° C and the resulting 2-nitro-4,6-dichloro-5-methylphenol is filtered off and washed with ice water.

Melting point: 82 –84° C

Yield: 392 g (corresponding to 85% of theory)

EXAMPLE 3

1,260 kg of sulphuric acid (100% strength by weight) are initially filled into a 1 m³ kettle and 300 kg of 4-chloro-5-methylphenol are added at 50° C. The reaction mixture is kept at 50° C for 10 hours, whilst stirring, and is forced onto 3,200 kg of water which have been filled into a 6 m³ kettle. The chlorination is effected by passing 156 kg of chlorine, during 5 hours into the reaction mixture warmed to 55° C. The internal pressure is kept at 1.9 bars. To complete the reaction, the mixture is stirred for a further hour and is then cooled to 30° C. At this temperature, 200 kg of nitric acid (80% strength by weight) are added in the course of 3 hours and the mixture is stirred for 2 further hours to complete the reaction. Thereafter the reaction mixture is cooled to 10° C and the resulting 2-nitro-4,6-dichloro-5-methylphenol is filtered off and washed with ice water.

Melting point: 82 – 84° C.

Yield: 412 kg (corresponding to 84% of theory).

What is claimed is:

1. In a process for preparing 2-nitro-4,6-dichloro-5-methylphenol by sulfonation of 4-chloro-5-methylphenol to form 2-sulfo-4-chloro-5-methylphenol followed by chlorination of the 2-sulfo-4-chloro-5-methylphenol to 2-sulfo-4,6-dichloro-5-methylphenol with subsequent reaction of the 2-sulfo-4,6dichloro-5-methylphenol with nitric acid, the improvement which comprises carrying out the sulfonation at 40–100° C with concentrated sulfuric acid to form 2-sulfo-4-chloro-5-methylphenol, thereafter diluting the reaction mixture with water to sulfuric acid content of 20 to 30 percent, chlorinating the resulting 2-sulfo-4-chloro-5-methylphenol with chlorine at 45–60° C under a pressure of 1–3 bars gauge pressure to form 2-sulfo-4,6-dichloro-5-methylphenol.

2. Process of claim 1 wherein the sulfonation is carried out in an excess of sulfuric acid.

3. Process of claim 1, wherin the sulfonation is carried out with a 5 to 7 molar excess of sulfuric acid, relative to starting compound.

4. Process according to claim 1 wherin the process is performed without isolating any intermediate product which is subsequently reacted.

* * * * *